United States Patent [19]

Bauer et al.

[11] 4,400,467

[45] Aug. 23, 1983

[54] PROCESS OF USING XANTHOMONAS CAMPESTRIS NRRL B-12075 AND NRRL B-12074 FOR MAKING HETEROPOLYSACCHARIDE

[75] Inventors: Keith A. Bauer, Los Altos; Behzad Khosrovi, El Cerrito, both of Calif.

[73] Assignee: Standard Oil Company (Indiana), Chicago, Ill.

[21] Appl. No.: 251,831

[22] Filed: Apr. 7, 1981

Related U.S. Application Data

[63] Continuation of Ser. No. 167,892, Jul. 14, 1980, abandoned.

[51] Int. Cl.³ .................. C12P 19/06; C12N 1/20; C12R 1/64
[52] U.S. Cl. .................. 435/104; 435/253; 435/813; 435/910
[58] Field of Search .................. 435/104, 253, 910

[56] References Cited

U.S. PATENT DOCUMENTS 3,328,262  6/1967  Lindblom et al. ............... 435/104 X
3,485,719  12/1969  Rogovin ............................. 435/104

FOREIGN PATENT DOCUMENTS 7612448  5/1977  Netherlands .
2008138A  5/1979  United Kingdom .

OTHER PUBLICATIONS

Rogovin et al., Biotechnol. Bioeng., XII, pp. 75–83, 1970.
Silman et al., Biotechnol. Bioeng. XIV, pp. 23–31, 1972.
Davidson, FEMS Microbiology Letters 3(1978) pp. 347–349.

*Primary Examiner*—Lionel M. Shapiro
*Attorney, Agent, or Firm*—Stephen R. May; Fred E. Hook

[57] ABSTRACT

This invention involves the production of heteropolysaccharides such as xanthan gum by the continuous fermentation of suitable nutrient media with new degenerative resistant variants of *Xanthomanas campestris*. Fermentation is conducted in a nitrogen, sulfur or phosphorous limited nutrient medium containing glucose or a minimal medium plus yeast extract and glutamic acid, in a first fermenter to enhance cultural growth. After the limiting growth element (nitrogen, sulfur or phosphorous) has been essentially consumed, the medium is then transferred to a second fermenter and fermentation continued while adding a suitable carbohydrate which the bacteria convert into the heteropolysaccharide product. The process may be modified by carrying out cultural growth and production of the polysaccharide in the same fermenter. The bacteria employed were cultured from a glucose-mineral salts medium fortified with yeast extract or a glucose-defined minimal medium in which ammonium chloride served as the sole assimilable nitrogen source.

17 Claims, No Drawings

PROCESS OF USING XANTHOMONAS CAMPESTRIS NRRL B-12075 AND NRRL B-12074 FOR MAKING HETEROPOLYSACCHARIDE

This is a continuation of application Ser. No. 167,892, filed July 14, 1980, abandoned.

INTRODUCTION

The present invention relates to a method for production of high molecular weight heteropolysaccharide polymers by the action of novel *Xanthomonas campestris* strains on a suitable nutrient medium.

A process for the cultivation of microorganisms of the type herein contemplated usually comprises their growth under aerobic conditions in an aqueous growth medium comprising, in addition to the carbon source, various nutrients such as assimilable sources of nitrogen and essential mineral salts.

BACKGROUND OF THE INVENTION

Earlier work has indicated that heteropolysacharrides produced by the action of Xanthomonas bacteria on carbohydrate media have potential applications as film forming agents, as thickeners for body building agents in edible products, cosmetic preparations, pharmaceutical vehicles, oil field drilling fluids, fracturing liquids and similar compositions and as emulsifying, stabilizing and sizing agents. Heteropolysacharrides, particularly xanthan gum, have significant potential as a mobility control agent in micellar polymer flooding. Xanthan gum has excellent viscosifying properties at low concentration, is resistant to shear degradation and exhibits only minimal losses in viscosity as a function of temperature, pH, and ionic strength. For these reasons, xanthan gum is an attractive alternative to synthetic polyacrylamides for enhanced oil recovery operations.

Fermentation of the inoculated medium with Xanthomonas organisms for 36 to 72 hours under aerobic conditions results in the formation of xanthan gum which is separated from the other components of the medium by precipitation with acetone or methanol in a known manner. Because of time required to ferment each batch, the low biopolymer content of the fermented medium and the processing required for the recovery and purification of the product, xanthan is relatively expensive.

Other investigators have produced xanthan heteropolysacharrides by means of single stage or multistage "continuous" fermentation. In most instances, *Xanthomonas campestris* was grown in a medium containing dried distillers solubles (DDS) or other complex nutrient as a source of nitrogen and growth factors. There has been no instance of which we are aware, however, that xanthan was produced by single stage continuous fermentation with *Xanthomonas campestris* using a chemically defined synthetic medium containing only glucose, ammonium chloride as the sole nitrogen source, and mineral salts.

It is well known that the continuous production of xanthan has been hampered by a tendency of the culture (*Xanthomonas campestris*) to change or degenerate after a fairly short and specific number of turnovers, i.e., the time required to completely replace one volume of broth in the fermentation vessel, or the reciprocal of the dilution rate. Normally, 6 to 9 turnovers are the maximum that can be obtained before degeneration of the culture occurs. At the same time, there is a decrease in viscosity, a loss in volumetric productivity of xanthan, i.e., grams of xanthan per liter of broth per hour, and the appearance of a variety of culture variants or strains that no longer produce xanthan or else produce a poor quality of xanthan. It has been demonstrated that this phenomenon occurs when DDS is used as the complex nitrogen source, whether in the whole form or as a water soluble extract.

The most pertinent publications of which we are aware are as follows:

1. P. Rogovin et al,. 1970, "Continuous Fermentation to Produce Xanthan Biopolymers: Laboratory Investigation," *Biotechnol. Bioeng.*, XII, pages 75–83.

2. K. W. Silman, et al., 1972, "Continuous Fermentation to Produce Xanthan Biopolymer: Effect of Dilution Rate," *Biotechnol. Bioeng.*, XIV, pages 23–31.

3. P. Rogovin, U.S. Pat. No. 3,485,719, Continuous Production of Xanthan.

4. G. P. Lindblom, et al., U.S. Pat. No. 3,328,262, Heteropolysacharride Fermentation Process.

5. Netherlands patent application No. 7,612,448, Method for the Production of Bacterial Polysacharrides.

6. "Production of Polysaccharides by *Xanthomonas campestris* in Continuous Culture," FEMS Microbiology Letters 3 347–349 (1978) by I. W. Davidson.

7. Process for the Production of Xanthan Gum, British patent application No. 2,008,138A (Tate and Lyle Ltd.)

SUMMARY OF THE INVENTION

Briefly, we have developed a process and discovered media compositions that lend themselves well to continuous fermentation when such media are inoculated with novel *Xanthomonas campestris* strains discovered by us.

Thus, our invention concerns a process for the simultaneous or sequential production of microorganisms and polysaccharides which comprises continuously cultivating a carbohydrate—utilizing microorganism under aerobic conditions in a single stage continuous fermenter under conditions such that production of heteropolysaccharide is maximized in relation to cell production. Alternatively, a two stage continuous fermenter system may be employed wherein the first stage is operated in order to maximize production of microorganisms which are then fed into the second stage operated under conditions optimum for heteropolysaccharide production. The liquid growth medium consists essentially of the carbon and energy source together with assimilable sources of nitrogen, essential mineral salts and special nutrients. These are fed continuously to the fermenter either in a single growth medium comprising all the nutrients in balanced quantities in an aqueous mixture or in the form of a multiple feed stream system comprising the nutrients broken down into streams containing individual nutrients or groups of nutrients.

The main advantage of the process of our invention is its use of appropriate culture conditions and a correctly balanced nutrient mixture in order to maximize production of the desired heteropolysaccharide product in relation to unwanted microorganisms and in order to maximize the long term stability of the system. The use of continuous culture maximizes volumetric throughput, thereby decreasing capital expenditure and certain operating costs.

In carrying out the process of our invention, we employ novel strains of *Xanthomonas campestris*, designated *Xanthomonas campestris* L3 NRRL B-12074 and

*Xanthomonas campetris* L5 NRRL B-12075. These strains are stable under continuous fermentation conditions and produce high quality xanthan gum in continuous flow culture under specified process conditions. By the expression "high quality xanthan" we means a gum which at any given concentration has a viscosity at least as high as that of gum produced by conventional bath fermentation. We have found that these strains of *Xanthomonas campestris* arise spontaneously, depending upon the conditions of growth and are for the purpose of our invention identified by their colony morphology on solid (agar) plate growth media and their ability to grow and produce gum in liquid media. The growth media are comprised of glucose as a source of energy and carbon; assimilable nitrogen; and essential minerals such as phosphorous, potassium, sulfur, magnesium and iron as well as other elements required in trace amounts.

PREFERRED EMBODIMENTS OF THE INVENTION

Subcultures of these living organisms can be obtained upon request from the permanent collection of the Northern Regional Research Laboratories, Agricultural Research Services, U.S. Department of Agriculture, Peoria, IL., U.S.A. The accession numbers in this repository for the L3 and L5 strains are given above. The liquid growth medium employed in carrying out the present invention comprises a nitrogen-containing compound which may, for example, be ammonia, urea, an ammonium salt (for example, ammonium sulfate or ammonium chloride), nitric acid or a nitrate (for example, an alkali metal nitrate). Additionally, the nitrogen requirement of the microorganisms may be partially or completely satisfied by the use of a complex source of nitrogen, for example, yeast extract, yeast autolysate, distiller's dried solubles, or corn-steep liquor.

Other elements which may be present in the medium include phosphorous, potassium, sulfur, magnesium and iron. Phosphorous may be in the form of one or more phosphates or phosphoric acid and, preferably, present in a concentration from about 0.1 to 2.0 g/l. The potassium source may be in the form of a salt or as potassium hydroxide and is preferably present in a concentration of from about 0.040 to 1 g/l. The sulfur source may be sulfuric acid or a sulfate and suitably is present in a concentration of 4 to 100 mg/l. Magnesium, as a salt, preferably is present in a concentration of 4 to 50 mg/l. Iron is preferably added as $FeSO_4 \cdot 7 H_2O$ in a concentration of 1 to 15 mg/l. The medium may also contain trace amounts of other elements in the form of suitable salts, for example, calcium, zinc, manganese, boron, cobalt, molydenum and copper. In order to avoid precipitation of mineral salts, a chelating agent such as citric acid, a salt of citric acid, or ethylene diamine tetra-acetic acid may be included in the medium. When citric acid is used for this purpose, its concentration in the medium is preferably in the range from about 0.02 to 1 gm/l.

The process of this invention is preferably carried out in continuous flow culture for which a suitably adapted fermentation vessel, for example, a stirred baffled fermenter, may be used. This vessel is provided with a means of continuously pumping in nutrient streams and continuously withdrawing product in the form of a mixture of heterpolysaccharides and cells in spent medium. The source of oxygen is air, essentially pure oxygen or a mixture of these gases, and may be contacted with the culture preferably by bubbling continuously through a sparger at the base of the vessel such that the dissolved oxygen concentration is maintained in the range of 10 to 100% or preferably 20 to 60% of the air saturation.

The temperature of the culture is generally maintained between 20° and 60° C., preferably between 25° and 30° C. The pH of the culture is controlled at a pH between 4.0 and 8.0 and preferably 6.0 and 7.0, by the appropriate addition of an alkali, for example, sodium hydroxide, potassium hydroxide, ammonium hydroxide, and/or an acid, for example, sulfuric acid or phosphoric acid.

The culture is started by growing the microorganism through a series of inoculation stages. The stored microorganism either in freeze dried form, in the form of frozen culture or in the form of a slow growing culture on solid (agar) medium, is transferred to a small volume of liquid medium and inoculated under appropriate conditions. Actively growing cells are maintained in this manner by sequential transfers into progressively increasing volumes of culture until a sufficient quantity of cells is available for inoculation of the fermenter. After inoculation of the fermenter, with the initial cell density is preferably in the range of from 0.05 to 0.5 g (dry weight)/l, growth is allowed to proceed batchwise. During this stage, the supply of oxygen may be augmented with carbon dioxide, preferably in a concentration of from about 1 to about 5% by volume, in order to minimize the lag phase of growth common at this time of inoculation. The switch to continuous flow is made at a time when the cell density has achieved a concentration near that expected to be maintained in subsequent steady state operation, but prior to the time when nutrients will be exhausted.

Our invention may be further illustrated by the specific examples that follow. The first two examples illustrate a method of isolation and characterization of novel *Xanthomonas campestris* strains capable of stable gum production in continuous culture operation using: (1) a basically glucose-mineral salts medium with the addition of small quantities of yeast extract and sodium glutamate to produce a new strain designated *Xanthomonas campestris* L3 NRRL B-12074, and (2) a second medium comprising only glucose and mineral salts to produce a second strain designated *Xanthomonas campestris* L5 NRRL B-12075, capable of good growth and gum production.

EXAMPLE I

A single colony of *Xanthomonas campestris* NRRL B-1459, for the purposes of this description designated L1, was cultured aerobically at 28° C. in a shaken flask batch culture, using a suitably adapted glucose-mineral salts medium augmented with 0.04% yeast extract. This culture was transferred sequentially into progressively increasing volumes of medium until a sufficient volume of culture for inoculation of a 3 liter capacity fermenter was obtained.

The fermenter containing the medium listed in Table II was inoculated to an initial cell density of 0.06 g dry weight cells/liter. The temperature of the culture was controlled at 28° C., and its pH held at 7.0 using 10% sodium hydroxide. The culture was agitated by means of stirring and aerated by the introduction of sterile air augmented with 2% carbon dioxide at such flow rates that the dissolved oxygen concentration was maintained above 20% of air saturation. Twenty-five hours after inoculation, the cell density had reached 1.7 g/l (dry weight) and operation of the fermenter was switched to continuous flow using a medium similar to that described in Table II. Once continuous operation was established, the carbon dioxide flow was discontinued. Continuous flow operation was maintained by continuously feeding in fresh sterile medium similar to that described in Table II and at the same time withdrawing culture containing cells and xanthan gum at essentially the same flow rate. The balance of nutrients in the medium was such that nitrogen limits the growth of the cells. The medium flow rate was adjusted such that the dilution (or inverse of residence time) was 0/09 hr$^{-1}$. During the course of continuous flow operation the concentration of glucose in the feed medium was increased progressively to 30 g/l, the equivalent ammonia concentration in the feed increased to 32 mM, and the pH of the culture decreased to pH 6.5.

Continuous flow was maintained for a period of time in excess of 1,150 hours or 103 reactor volumes. It was found that 3 strains, designated M1, S1 and L3, appeared in the culture, with the strain L3 eventually exclusively dominating the culture. The time course of this development of these strains is shown in Table 1.

TABLE I

| Time After Inoculation of Fermenter (Hours) | % of Viable Cells | | | |
|---|---|---|---|---|
| | L1 | M1 | S1 | L3 |
| 25 | 100 | — | — | — |
| 71 | 100 | — | — | — |
| 145 | 100 | — | — | — |
| 170 | 97 | 3 | — | — |
| 195 | 95 | 5 | — | — |
| 216 | 88 | 12 | 1 | — |
| 239 | 79 | 19 | 1 | — |
| 289 | 61 | 32 | 4 | 3 |
| 339 | 47 | 38 | 8 | 7 |
| 364 | 38 | 42 | 10 | 10 |
| 458 | 27 | 23 | 16 | 34 |
| 503 | 22 | 16 | 12 | 50 |
| 552 | 24 | 6 | 14 | 55 |
| 624 | 15 | 2 | — | 81 |
| 701 | 12 | — | — | 86 |
| 818 | — | — | — | 100 |

Subsequent to 818 hours, only strain L3 could be detected in the culture. Strains of microorganisms were identified by their colony morphology on solid medium on bacterialogical plates as well as by their performance in both (liquid medium) in shaken flasks after incubation at 28° C. Characteristics of these strains are shown in Table III. The two types of media used were designated XA2, a glucose mineral salts medium containing 0.04% yeast extract; and YM, a general purpose bacterialogical medium available commercially from Difco Laboratories, Detroit, Mich., USA. The composition of these media is described in Table IV.

The steady state performance of the fermenter was measured at 1,106 hours after initial inoculation. Cell density (dry weight) was measured to be 4.08 g/l and the concentration of xanthan gum measured to be 9.32 g/l with a viscosity of 2940 cp. Corresponding volumetric productivity was 0.86 gram xanthan gum per liter of fermenter culture volume per hour.

TABLE II

| Glucose* | 20 g/l |
|---|---|
| Yeast Extract | 0.4 g/l |
| Sodium Glutamate | 0.02 g/l |
| NH$_4$Cl | 16 mM |
| KH$_2$PO$_4$ | 5 mM |
| K$_2$SO$_4$ | 1 mM |

TABLE II-continued

| MgSO$_4$ | 0.5 mM |
|---|---|
| CaCl$_2$ | 0.1 mM |
| FeSO$_4$* | 20 μM |
| ZnSO$_4$ | 2.5 μM |
| MnSO$_4$ | 2.5 μM |
| H$_3$BO$_3$ | 2.5 μM |
| CuSO$_4$ | 1.0 μM |
| Na$_2$MO | 1.0 μM |
| CoCl$_2$ | 1.0 μM |
| KI | 1.9 μM |
| Citric Acid | 0.5 mM |

*Glucose and FeSO$_4$ were sterilized separately before adding to the main medium.

EXAMPLE II

A number of strains of *Xanthomonas campestris* were isolated from solid media plates prepared from continuous culture samples and tested for their ability to produce high viscosity gum in batch cultures using glucose-mineral salts medium augmented with a small quantity of yeast extract. The medium used was XA2 as described in Table III. One such strain, designated *Xanthomonas campestris* L5 NRRL 12075, was selected for its ability to produce a higher viscosity than other strains. After 48 hours of incubation at 28° C. in such medium, variant L5 produced a viscosity of 1900 cp compared to 700-800 cp for L1 and 400-500 cp for L3 but grew more slowly in simple mineral salts medium than L3.

When tested in media containing only glucose and mineral salts, it was discovered that this strain was capable of good growth and gum production. Strain L5 was further tested in continuous culture in a fermenter using the following medium:

| Glucose | 30 g/l |
|---|---|
| NH$_4$Cl | 30 mM |
| H$_3$PO$_4$ | 50 mM |
| K$_2$SO$_4$ | 0.3 mM |
| KCl | 1 mM |
| MgCl$_2$ | 0.5 mM |
| CaCl$_2$ | 0.1 mM |
| FeSO$_4$ | 20 mM |
| Trace Elements | As in Table II, but at twice the concentration |

The balance of nutrients in this medium was such that sulfur limited the growth of the microorganisms. The temperature of the fermenter was controlled at 28° C. and its pH controlled at 6.5 using 10% sodium hydroxide. Air was supplied at such a rate to maintain the concentration of dissolved oxygen above 20% of air saturation. The flow of medium was adjusted to achieve a dilution rate of 0.06 hr$^{-1}$. Performance of this strain under continuous fermentation conditions measured in terms of its production of xantham gum yielded a concentration of 8.1 grams of gum per liter with a viscosity of 2360 cp. The viscosity of the fermented media in all cases was measured on a Brookfield LVT Viscometer, using a number 4 spindle at 30 rpm.

Growth Behavior and Gum Production of Parent and L3 and L5 Strains in Flask Culture Strains were grown in liquid culture in shaken flasks in both YM and glucose-mineral salts medium (XA2/50) for 48 hours. All strains were viscous in YM medium. Performance in XA2/50 medium:

Parent: Shows biphasic growth; viscosity, 700-800 cps; xanthan gum concentration, 4-5 g/l.

L3: Shows rapid pH drop during growth; viscosity 400–500 cps; xanthan gum concentration, 4 g/l.

L5: Grows more slowly than either parent or L3; viscosity, 1900 cps; xanthan gum concentration not determined.

Performance in Continuous Culture

Parent: Unstable during nitrogen-limited continuous culture generally leading to loss of ability to produce gum.

L3: Shows stable gum production in continuous culture for extended periods of time under nitrogen limited conditions. Requires 10% of its nitrogen source (ammonia) to be augmented with yeast extract for maximum gum production.

L5: Stable in continuous culture in defined glucose-ammonia-mineral salts medium without addition of complex nitrogem. Produces high viscosity under sulfur-limited conditions.

TABLE III

Composition of XA2 and YM media.

Medium XA2:

| | |
|---|---|
| Glucose | 20 g/l |
| NH4Cl | 16 mM |
| Yeast Extract | 0.4 g/l |
| KH2PO4 | 50 mM |
| K2SO4 | 1 mM |
| MgSO4 | 0.5 mM |
| CaCl2 | 0.1 mM |
| FeSO4 | 20 μM |
| Trace Elements | as in Table II |
| Sodium Citrate | 0.5 mM |
| pH Adjusted to 7.0 with NaOH | |
| For solid medium - Add agar to | 20 g/l |

Medium YM:

| | |
|---|---|
| Bacto Yeast Extract | 3 g/l |
| Malt Extract, Difco | 3 g/l |
| Bacto Peptone | 5 g/l |
| Bacto Dextros | 10 g/l |
| For solid medium - add agar to | 20 g/l |

The variant strains produced in Examples 1 and II are characterized as follows:

TABLE IV

| Variant Designation | Colony Morphology on Solid Media After 4 Days Incubation at 28° C. | Performance in Batch Flask Culture After 48 Hours of Incubation at 28° C. |
|---|---|---|
| Parent Strain (L1) | XA2: mucoid, 4–5 mm base diam. YM: mucoid, 7 mm base diam. yellow pigmentation | viscous in YM broth XA2: xanthan, 4–5 g/l viscosity, 700–800 cp |
| M1 | XA2: mucoid, 2 mm diam. YM: mucoid, 4 mm diam. more pigmented than L1 | viscous in YM broth XA2: xanthan, 2 g/l not viscous |
| S1 | XA2: small non-mucoid yellow colonies, flattened out in center | not viscous in YM broth nor in XA2 |
| L3 | XA2: mucoid, 6 mm diam. YM: mucoid, 8 mm diam. less pigmented than L1 | viscous in YM broth XA2: xanthan, 4 g/l viscosity, 400–500 cp |
| L5 | XA2: mucoid, 5–6 mm diam., pigmentation same as L3, light yellow YM: mucoid 9–10 mm diam., pigmentation same as L3, light yellow | |

EXAMPLE III

In this example, a strain which we designated *Xanthamonous campestris* L3 was employed. The parent strain of *Xanthomonas campestris* was obtained from the Northern Regional Research Center, U.S.D.A., Peoria, Ill., and is identified by their number NRRL B-1459, as well as by the American Type Culture Collection number ATCC 13951. The strain used in this example was isolated from the parent strain using techniques discussed in the foregoing description and, in particular, referred to in Example 1.

Variant L3 was selected for continuous flow culture according to the method described above and is notable for its stability in continuous culture and its ability to produce high quality gum. This strain was maintained in a steady state continuous flow culture using the following sterile medium:

| STREAM 1 - MAIN MEDIUM | |
|---|---|
| Glucose | 30 gm/l |
| NH4Cl | 0.86 gm/l |
| KH2PO4 | 0.68 gm/l |
| K2SO4 | 0.17 gm/l |
| MgSO4 .7H2O | 0.12 gm/l |
| CaCl2.2H2O | 0.015 gm/l |
| Difco Yeast Extract | 0.4 gm/l |
| Sodium glutamate | 0.02 gm/l |
| FeSO4.7H2O | 5.6 mg/l |
| Trace Element Mixture | 1.0 ml/l |
| Citric Acid | 0.1 gm/l |

The trace element mixture used was a concentrated source of these elements and contained $ZnSO_4$, $MnSO_4$ and $H_3BO_3$, each at 2.5 mM; $CuSO_4$, $Na_2Mo_4$, $CoCl_2$, and KI, each at 1.0 mM; together with 1.0 mM $H_2SO_4$ to prevent precipitation.

| STREAM 2 - SUPPLEMENTAL AMMONIA | |
|---|---|
| Ammonium Hydroxide | 1.0 Molar |

The folowing fermenter conditions and medium flow rates were effective when steady state measurements were made after 935 hours of continuous operation:

| | |
|---|---|
| Fermenter working volume | 3.2 liters |
| Temperature | 32° C. |
| pH | 6.4 |
| pH control alkali | 10% NaOH |
| Stirring rate | 700 rpm |
| Air flow rate | 1.0 liter/minute |
| Stream 1 | 285.3 ml/hour |
| Stream 2 | 4.68 ml/hour |
| Culture outflow | 288.2 g/hour |

Analysis of the fermenter yielded the following results:

| | |
|---|---|
| Dissolved Oxygen | 15% of air saturation |
| Residual Glucose | 5.53 g/l |
| Residual Ammonium Ion | <0.08 mM |
| Cell Density | 4.21 gm/l |
| Xanthan concentration | 9.58 gm/l |
| Viscosity | 3000 cp |

Using the above, the following parameters of performance were calculated:

| | |
|---|---|
| Dilution Rate (inverse of residence time) | 0.09 hr.$^{-1}$ |
| Glucose uptake | 6.97 gm/hr. |
| Xanthan output | 2.76 gm/hr. |

| -continued | |
|---|---|
| Cell output | 1.21 gm/hr. |
| Xanthan yield | 0.40 g/g glucose used |
| Xanthan specific production | 0.20 g/g cells/hr |
| Xanthan volumetric productivity | 0.86 g/l/hr |

Cell density (dry weight) was measured after centrifuging by gravimetric means. Xanthan density was measured gravimetrically after centrifuging to remove cells, precipitation using ethanol and drying. Viscosity was measured on a Brookfield LVT Viscometer, using using a No. 4 spindle at 30 rpm and at room temperature, (25° C.).

The medium balance in this example was such that the nitrogen supply limited the growth of the microorganisms with all other nutrients in operating excess. The yeast extract supplied 6.6% of the cells' nitrogen requirement; sodium glutamate supplied 0.3% of the cells' nitrogen requirement, with the remainder being provided by ammonium chloride and ammonium hydroxide.

EXAMPLE IV

Another strain, Xanthomonas campestris strain L5 was tested for its ability to produce gum in continuous culture using a glucose defined minimal medium, namely one in which neither yeast extract nor sodium glutamate was added, but in which ammonium chloride provided the sole source of nitrogen. Strain L5 was selected for its ability to grow in such defined medium and was obtained in the manner described in Example II above. It was grown through a series of innoculum preparation stages but in suitably adapted glucose-mineral salts media prior to transfer to continuous flow operation.

The following nutrient medium was used for continuous flow:

| | |
|---|---|
| Glucose | 30 gm/l |
| NH$_4$Cl | 30 mM |
| H$_3$PO$_4$ | 50 mM |
| K$_2$SO$_4$ | 0.3 mM |
| KCl | 1.0 mM |
| MgCl$_2$ | 0.5 mM |
| CaCl$_2$ | 0.1 mM |
| FeSO$_4$ | 20 µM |
| Trace Element Mixture | 2 ml/l |

Glucose and ferrous sulfate were separately sterilized. The trace element mixture was the same as used in Example III. The balance of nutrients in this medium was such that sulfur limited the growth of the microorganisms.

The following fermeter conditions were used:

| | |
|---|---|
| Fermenter Working Volume | 3.65 liters |
| Temperature | 28° C. |
| pH | 6.5 |
| pH control alkali | 10% NaOH |
| Stirring rate | 700 rpm |
| Air flow rate | 1.0 liter/min |
| Medium inflow | 202 ml/hr |
| Culture outflow | 210 g/hr |

The culture was analyzed with the following results:

| | |
|---|---|
| Dissolved oxygen | 35% |
| Residual glucose | 12.0 gm/l |

| -continued | |
|---|---|
| Residual ammonium ion | 3.0 mM |
| Cell density (dry weight) | 3.0 gm/l |
| Xanthan concentration | 8.1 gm/l |
| Viscosity | 2360 cp |

From these data, the following parameters of performance were calculated:

| | |
|---|---|
| Dilution Rate | 0.06 hr$^{-1}$ |
| Glucose uptake | 3.5 gm/hr. |
| Xanthan output | 1.7 gm/hr. |
| Cell output | 0.63 gm/hr. |
| Xanthan yield | 0.48 gm/g glucose used |
| Xanthan specific productivity | 0.16 gm/gm cells/hr |
| Xanthan volumetric productivity | 0.47 gm/l/hr |

As illustrated in the foregoing examples and description, our invention is directed to a continuous fermentation process to produce heteropolysaccharides such as xanthan gum, by the action of new degenerative resistant strains of Xanthomonas campestris. Although we have mentioned by way of example the glucose-mineral salts medium, sometimes referred to as a minimal medium, and a minimal medium containing yeast extract with or without sodium glutamate, it is to be understood that we may employ the aforesaid novel strains in any suitable liquid medium containing assimilable sources of carbon, an undefined nitrogen source and inorganic substances.

We claim:

1. A method for the production of a heteropolysaccharide by means of continuous fermentation which comprises innoculating a liquid carbohydrate minimal medium with a degenerative resistant strain of Xanthomonas campestris selected from the group consisting of Xanthomonas campestris L3 and Xanthomonas campestris L5, having the identifying characteristics of NRRL B-12074 and NRRL B-12075, respectively, cultivating said strain in said medium without discontinuing the fermentation process, withdrawing the results fermented medium therefrom at a rate such that an essentially steady state condition is maintained and recovering heteropolysaccharide from said fermented medium.

2. A novel continuous process for preparing a heteropolysaccharide which comprises continuously cultivating a degenerative resistant microorganism selected from the group consisting of Xanthomonas campestris L3 and Xanthomonas campestris L5, having the identifying characteristics of NRRL B-12074 and NRRL B-12075, respectively, under aerobic conditions in a liquid nutrient medium wherein the growth limiting nutrient is any of the nutrients normally used in said process so that the production of microorganisms is maximized, thereafter continuously feeding the microorganisms thus produced in said medium to a second stage into which a fermentable sugar is fed whereby the formation of heteropolysaccharide in said second stage is maximized.

3. A novel continuous process for preparing a heteropolysaccharide which comprises cultivating a degenerative resistant microorganism strain selected from the group consisting of Xanthomonas campestris L3 and Xanthomonas campestris L5 having the identifying characteristics of NRRL B-12704 and NRRL B-12075, respectively, in a liquid carbohydrate nutrient minimal medium containing a complex undefined nitrogen source under aerobic conditions, wherein said medium is continuously fed to a fermentation zone and a culture of one of said strains containing said heteropolysaccharide is continuously withdrawn therefrom.

4. The process of claim 1, wherein said minimal medium contains a complex undefined source of nitrogen.

5. The process of claim 2 wherein the limiting nutrient in said liquid medium is nitrogen.

6. Process of claim 2 wherein the limiting nutrient in said liquid medium in phosphorous.

7. Process of claim 2 wherein the limiting nutrient in said liquid medium is sulfur.

8. Process of claim 1 in which the heteropolysaccharide is xanthan and the carbohydrate is glucose.

9. Process of claim 1 wherein said liquid medium is a glucose-defined mineral salts medium containing a complex undefined nitrogen source.

10. Process of claim 9 wherein said undefined nitrogen source is yeast extract.

11. Process of claim 9 wherein said undefined nitrogen source is yeast autolysate.

12. Process of claim 1 wherein the degenerative resistant strain employed is *Xanthomonas campestris* B-12074.

13. Process of claim 1 wherein the degenerative resistant strain employed is *Xanthomonas campestris* B-12075.

14. A culture consisting essentially of *Xanthomonas campestris* L3 NRRL B-12074.

15. A culture of a bacterial strain consisting essentially of *Xanthomonas campestris* NRRL L3 B-12074, said strain being stable and capable of xanthan gum production in continuous fermentation conditions in a nutrient media comprising assimilable sources of carbon, nitrogen, and essential minerals.

16. A culture consisting essentially of *Xanthomonas campestris* L5 NRRL B-12075.

17. A culture of a bacterial strain consisting essentially of *Xanthomonas campestris* L5 NRRL B-12075, said strain being stable and capable of xanthan gum production in continuous fermentation conditions in a nutrient media comprising assimilable sources of carbon, nitrogen, and minerals.

* * * * *

UNITED STATES PATENT OFFICE
CERTIFICATE OF CORRECTION

PATENT NO. : 4,400,467
DATED : August 23, 1983
INVENTOR(S) : Keith Alan Bauer and Behzad Khosrovi It is certified that error appears in the above-identified patent and that said Letters Patent are hereby corrected as shown below:

Column 3, line 5, "means" should read --mean--;

line 7, "bath" should read --batch--.

Column 5, line 12, "0/09 $hr^{-1}$" should read --0.09 $hr^{-1}$--;

line 47, "both" should read --broth--.

Column 8, line 62, after the word "above" insert --data--.

Column 9, line 53, "fermeter" should read --fermenter--.

Column 10, line 42, "results" should read --resulting--;

line 66, "B-12704" should read --B-12074--.

Signed and Sealed this

Twenty-ninth Day of January 1985

[SEAL]

Attest:

DONALD J. QUIGG

Attesting Officer     Acting Commissioner of Patents and Trademarks